United States Patent
Shintani et al.

(10) Patent No.: US 9,341,640 B2
(45) Date of Patent: May 17, 2016

(54) APPARATUS FOR MULTIPLE AUTOMATIC ANALYSIS OF BIOSAMPLES, METHOD FOR AUTOANALYSIS, AND REACTION CUVETTE

(75) Inventors: Etsurou Shintani, Tokyo (JP); Akira Goukura, Tokyo (JP); Kenichi Yokota, Tokyo (JP); Minoru Ogura, Tokyo (JP)

(73) Assignee: MITSUBISHI KAGAKU IATRON, INC., Tokyo (JP)

( * ) Notice: Subject to any disclaimer, the term of this patent is extended or adjusted under 35 U.S.C. 154(b) by 1164 days.

(21) Appl. No.: 11/910,408

(22) PCT Filed: Apr. 3, 2006

(86) PCT No.: PCT/JP2006/307040
§ 371 (c)(1),
(2), (4) Date: Oct. 1, 2007

(87) PCT Pub. No.: WO2006/107016
PCT Pub. Date: Oct. 12, 2006

(65) Prior Publication Data
US 2008/0318323 A1 Dec. 25, 2008

(30) Foreign Application Priority Data
Apr. 1, 2005 (JP) ................ 2005-105700

(51) Int. Cl.
*G01N 21/03* (2006.01)
*B01L 3/00* (2006.01)
(Continued)

(52) U.S. Cl.
CPC ............ *G01N 35/025* (2013.01); *B01L 3/5082* (2013.01); *B01L 2200/025* (2013.01); *B01L 2300/0851* (2013.01); *Y10T 436/113332* (2015.01)

(58) Field of Classification Search
CPC ........ G01N 35/025; G01N 21/07; B01L 3/50; B01L 3/5082; B01L 2200/025; B01L 2300/0851; Y10T 436/113332
USPC ............ 422/64, 65, 68.1, 62, 63, 100, 99, 50, 422/52, 82, 547–550; 73/1; 436/43–47, 436/136; 356/246, 409, 410, 411; D24/224
See application file for complete search history.

(56) References Cited

U.S. PATENT DOCUMENTS 4,560,269 A * 12/1985 Baldszun et al. ............. 356/246
4,766,078 A 8/1988 Gang
(Continued)

FOREIGN PATENT DOCUMENTS

CN 1115027 A 1/1996
EP 0628822 12/1994
(Continued)

OTHER PUBLICATIONS

Machine Translation of Ogura (JP 2001-013151) p. 1-7.*
(Continued)

*Primary Examiner* — Lyle Alexander
*Assistant Examiner* — Robert Eom
(74) *Attorney, Agent, or Firm* — Heslin Rothenberg Farley & Mesiti P.C.; Kristian E. Ziegler

(57) ABSTRACT

A biosample autoanalyzer including: a sample supply unit having a plurality of biosamples; a first measuring unit fitted with a first optical measuring device; a sample transport capable of transporting the biosamples from the sample supply unit to the reaction cuvettes on the first measuring unit; a second measuring unit fitted with a second optical measuring device; a cuvette transfer device capable of transferring the reaction cuvettes to the second measuring unit; a reagent supply unit having reagents; and (7) a reagent transport device capable of transporting reaction reagents to the reaction cuvettes. The analyzer is operated wherein the reaction cuvettes on the second measuring unit are dispensed with the biosamples on the first measuring unit, subsequently transferred from the first measuring unit to the second measuring unit by the cuvette transfer device, such that different measurements are carried out by the first measuring unit and the second measuring unit.

31 Claims, 9 Drawing Sheets

(51) Int. Cl.
   *B01L 3/14*     (2006.01)
   *G01N 35/02*    (2006.01)

(56) References Cited

U.S. PATENT DOCUMENTS

| | | | |
|---|---|---|---|
| 5,120,503 A * | 6/1992 | Hinckley et al. | 422/527 |
| 5,843,376 A | 12/1998 | Ishihara et al. | |
| 6,117,683 A | 9/2000 | Kodama et al. | |
| 6,562,298 B1 * | 5/2003 | Arnquist et al. | 422/63 |
| 6,599,749 B1 | 7/2003 | Kodama et al. | |
| 7,138,091 B2 | 11/2006 | Lee et al. | |
| 7,341,691 B2 * | 3/2008 | Tamura et al. | 422/64 |
| 2003/0049170 A1 | 3/2003 | Tamura et al. | |
| 2003/0049171 A1 * | 3/2003 | Tamura et al. | 422/64 |
| 2004/0057872 A1 * | 3/2004 | Shibuya et al. | 422/64 |
| 2004/0096960 A1 * | 5/2004 | Burd Mehta et al. | 435/287.2 |
| 2005/0013746 A1 | 1/2005 | Lee et al. | |

FOREIGN PATENT DOCUMENTS

| | | |
|---|---|---|
| EP | 0661532 | 7/1995 |
| JP | 60122865 U | 8/1985 |
| JP | 03-102262 | 4/1991 |
| JP | 3102262 A | 4/1991 |
| JP | 526883 A | 2/1993 |
| JP | 9222429 A | 8/1997 |
| JP | 9281113 A | 10/1997 |
| JP | 20014636 A | 1/2001 |
| JP | 200113151 A | 1/2001 |
| JP | 2001013151 A * | 1/2001 |
| JP | 200383992 A | 3/2003 |
| JP | 2004-101295 | 4/2004 |
| JP | 2004-309136 | 11/2004 |
| JP | 2006107016 A1 | 10/2006 |
| WO | WO93/03383 | 2/1993 |
| WO | WO03/090897 | 11/2003 |

OTHER PUBLICATIONS

International Search Report for parent PCT Application PCT/JP2006/307040 (published as WO2006/107016) mailed Jul. 18, 2006.
Japanese Written Opinion for parent international PCT application No. PCT/JP2006/307040, mailed on Jul. 18, 2006.
English translation of above Written Opinion for parent international application No. PCT/JP2006/307040.
Supplemental European Search Report and Opinion for European Patent Appl. No. EP06730988, mailed Jul. 3, 2015.

* cited by examiner

APPARATUS FOR MULTIPLE AUTOMATIC ANALYSIS OF BIOSAMPLES, METHOD FOR AUTOANALYSIS, AND REACTION CUVETTE

CROSS-REFERENCE TO RELATED APPLICATIONS

This application is a §371 filing of PCT application PCT/JP2006/307040 filed on Apr. 3, 2006 which claims priority from Japanese application 2005-105700 filed on Apr. 1, 2005. The disclosures of these applications are included by reference herein in their entirety.

TECHNICAL FIELD

The present invention relates to an apparatus for a multiple automatic analysis of biosamples, a method for an autoanalysis, and a reaction cuvette.

BACKGROUND ART

Heretofore, an automatic analyzer for measuring components in biosamples, such as blood or urine samples, is predominately used in the measurements of biochemical items such as enzymes. Recently, however, there has been an increase in the measurements of immunological items, such as hormones or tumor markers. In a biochemical autoanalyzer, an absorbance change of a reaction liquid by a biochemical reaction in a blood sample is generally used to measure the substance to be examined by means of a transmitted or scattered light. Some immunological items can be measured by the biochemical autoanalyzer. For example, it has recently become possible to measure some immunological items which can be homogeneously measured without B/F separation, through an absorbance change in a latex agglutination method or the like.

On other hand, in a serum immunoanalyzer for immunological items, substances, such as hormones, to be examined in biosamples may be subject to a highly sensitive measurement by immunologically binding the substances to be examined in samples, and labeled antibodies or labeled antigens provided as reagents and prepared by labeling antibodies or antigens specifically reactive to each of the substances to be examined with a fluorescent colorant or the like, conducting a B/F separation, and then, detecting the labeled antibodies or labeled antigens by a heterogeneous measurement.

The recent development of a higher sensitivity in the serum immunoanalyzer has revealed the existence of substances, such as a thyroid-stimulating hormone, which indicate different pathologic conditions between the case of existing in a concentration higher than a normal level in blood, and the case of existing in a very small amount of less than a normal level in blood. Therefore, when measurements of biochemical items and immunological items for a same sample are required, a measurement by a biochemical autoanalyzer must be conducted after a measurement by a serum immunoanalyzer for the same sample, or alternatively, a measurement by a serum immunoanalyzer must be conducted after a measurement by a biochemical autoanalyzer for the same sample.

As above, in many cases, the test results obtained from a single autoanalyzer are insufficient for a diagnosis of clinical conditions. Therefore, an analyzing system capable of analyzing many items by a single system was proposed (for example, Patent Reference 1). However, the analyzing system proposed is composed of a plurality of biochemically analyzing units arranged along the line of transport of an analyte rack, that is, it has a structure substantially the same as that of plural biochemical autoanalyzers arranged in parallel.

Further, a multiple autoanalyzer with which a biochemical analyzing unit and an immunoanalyzing unit are integrated is known (for example, Patent Reference 2). In the multiple autoanalyzer, however, each of the biochemical analyzing unit and the immunoanalyzing unit is equipped with the reagent supply unit and devices in which reactions occur and are measured, respectively, and an analyte rack for supplying samples to the biochemical analyzing unit and the immunoanalyzing unit moves along the sample-transporting line, whereby the samples are shared. Therefore, the apparatus becomes large-scale, any advantage of saving space is limited, and a measuring and detecting time cannot be shortened.

The references cited abover correspeond to: [Patent Reference 1] Japanese Unexamined Patent Publication (Kokai) No. 9-281113, and [Patent Reference 2] Japanese Unexamined Patent Publication (Kokai) No. 2001-4636.

DISCLOSURE OF INVENTION

Problems to be Solved by the Invention

Therefore, the object of the present invention is to provide a means capable of realizing a single apparatus in which plural measurements having different analyzing accuracies, for example, a combination of biochemical analyses and immunological analyses, can be carried out, a small-scale apparatus in which parts thereof are shared, and a shortening of measuring time. Further, the inventors of the present invention succeeded in developing a reaction cuvette suitable for such an autoanalyzer, in the process of developing the above apparatus.

Means for Solving the Problems

The above object can be solved by the present invention, that is, an apparatus for a multiple automatic analysis of biosamples, characterized in that the apparatus comprises (1) a sample supply unit having a plurality of biosamples;

(2) a first measuring unit fitted with a first optical measuring means, the first measuring unit being capable of detachably holding, in a mutually independent manner, a plurality of reaction cuvettes independent from each other;

(3) a sample transport means capable of transporting the biosamples from the sample supply unit to the reaction cuvettes on the first measuring unit;

(4) a second measuring unit fitted with a second optical measuring means, the second measuring unit being capable of detachably holding, in a mutually independent manner, a plurality of reaction cuvettes independent from each other;

(5) a cuvette transfer means capable of transferring the reaction cuvettes on the first measuring unit to the second measuring unit;

(6) a reagent supply unit having reagents for use in a measurement by the first measuring unit and in a measurement by the second measuring unit; and (7) a reagent transport means capable of transporting reaction reagents, in mutually independent manner, from the reagent supply unit to the reaction cuvettes on the first measuring unit and/or the second measuring unit, wherein the reaction cuvettes on the second measuring unit are dispensed with the biosamples on the first measuring unit, and subsequently transferred from the first measuring unit to the second measuring unit by the cuvette transfer means to stand thereon; and wherein different measurements are carried out by the first measuring unit and the second measuring unit.

In a preferred embodiment of the present apparatus, the measurement by the first measuring unit and the measurement by the second measuring unit are different from each other with respect to a measuring principle or a detection mode. In a further preferred embodiment of the present apparatus, the measurement carried out by the second measuring unit has an accuracy higher than that of the measurement carried out by the first measuring unit.

In another preferred embodiment of the present apparatus, the measurement carried out by the first measuring unit is a biochemical or latex agglutination measurement, and the measurement carried out by the second measuring unit is an enzymatic immunoassay. In still another preferred embodiment of the present apparatus, each of the first measuring unit and the second measuring unit is a rotatable disc having a mounting zone capable of transporting the reaction cuvettes in a direction of rotation, in a peripheral region thereof, or a reciprocable plate having a mounting zone capable of transporting the reaction cuvettes in a direction of reciprocation.

In still another preferred embodiment of the present apparatus, the apparatus further comprises one or more additional measuring units fitted with an optical measuring means, and capable of detachably holding, in a mutually independent manner, a plurality of reaction cuvettes independent from each other, wherein a measurement different from those carried out on the first measuring unit and the second measuring unit is carried out thereby. In this embodiment, the reaction cuvettes on the additional measuring unit can be dispensed with the biosamples on the first measuring unit, and subsequently transferred from the first measuring unit to the additional measuring unit by the cuvette transfer means to stand thereon. Further, in this embodiment, the additional measuring unit may be a rotatable disc having a mounting zone capable of transporting the reaction cuvettes in a direction of rotation, in a peripheral region thereof, or a reciprocable plate having a mounting zone capable of transporting the reaction cuvettes in a direction of reciprocation. Further, in this embodiment, the measurement carried out by the first measuring unit may be a colorimetric or nephelometric measurement, the measurement carried out by the second measuring unit may be a chemiluminescent measurement, and the measurement carried out by the additional measuring unit may be a blood coagulation time measurement.

In still another preferred embodiment of the present apparatus, the apparatus further comprises one or more independent measuring units wherein the biosamples are supplied directly from the sample supply unit, and the measurement thereby can be conducted without a supply of any reagents from the reagent supply unit. In this embodiment, the independent measuring unit may be a unit for measuring body fluid electrolytes.

In still another preferred embodiment of the present apparatus, at least one of the above measuring units contains a means for detecting an abnormal sample.

In still another preferred embodiment of the present apparatus, the first optical measuring means in the first measuring unit, the second optical measuring means in the second measuring unit, and one or more optical measuring means in one or more additional measuring units are optical detectors different from each other. In this embodiment, the first optical measuring means in the first measuring unit, the second optical measuring means in the second measuring unit, and one of the optical measuring means in the additional measuring unit are optical detectors different from each other, and each of the detectors is any one of (1) an optical detector containing a light emission diode and a diode array,
(2) an optical detector containing a lamp unit and a spectrometer or
(3) an optical detector containing a photomultiplier as a photodetector.

In still another preferred embodiment of the present apparatus, the reagent supply unit contains a plurality of concentric-ring reagents-storing lanes which are independently rotatable in the same or counter directions and stoppable, and reagents to be supplied to the reaction cuvettes on the first measuring unit and the second measuring unit are stored in each of the concentric-ring reagents-storing lanes, respectively. In this embodiment, the reagent supply unit further may comprise a concentric-ring reagent storing lane in which reagents to be supplied to the reaction cuvettes on one or more additional measuring units are stored, and the reagent supply unit may further comprise a concentric-ring reagent storing lane in which reagents to be supplied to the reaction cuvettes on one or more independent measuring units are stored.

In still another preferred embodiment of the present apparatus, the reaction cuvette used has an arc mounting projection protruding from an upper sidewall of a cuvette main part. In this embodiment, the reaction cuvette may have, for example, a recess with a rounded wall surface on the bottom face of the cuvette main part, and may have a slot for the tip of a stirring rod, at the center of the recess. Further, in this embodiment, the reaction cuvette may have a fixing projection protruding downward from an undersurface of the mounting projection.

The present invention also relates to a method for a multiple automatic analysis of biosamples, by an apparatus for a multiple automatic analysis of biosamples, the apparatus comprising (1) a sample supply unit having a plurality of biosamples;
(2) a first measuring unit fitted with a first optical measuring means, the first measuring unit being capable of detachably holding, in a mutually independent manner, a plurality of reaction cuvettes independent from each other;
(3) a sample transport means capable of transporting the biosamples from the sample supply unit to the reaction cuvettes on the first measuring unit;
(4) a second measuring unit fitted with a second optical measuring means, the second measuring unit being capable of detachably holding, in a mutually independent manner, a plurality of reaction cuvettes independent from each other;
(5) a cuvette transfer means capable of transferring the reaction cuvettes on the first measuring unit to the second measuring unit;
(6) a reagent supply unit having reagents for use in a measurement by the first measuring unit and in a measurement by the second measuring unit; and
(7) a reagent transport means capable of transporting reaction reagents, in a mutually independent manner, from the reagent supply unit to the reaction cuvettes on the first measuring unit and/or the second measuring unit,
wherein the reaction cuvettes on the second measuring unit are dispensed with the biosamples on the first measuring unit, and subsequently transferred from the first measuring unit to the second measuring unit by the cuvette transfer means to stand thereon; and wherein different measurements are carried out by the first measuring unit and the second measuring unit.

Further, the present invention also relates to a reaction cuvette characterized in that a mounting projection protruding from an upper sidewall of a cuvette main part has an arc form. The preferred embodiment of the present cuvette has a recess with a rounded wall surface on the bottom face of the cuvette main part. Another preferred embodiment of the present cuvette has a slot for the tip of a stirring rod, at the center of the recess. Still another preferred embodiment of the present cuvette has a fixing projection protruding downward from an undersurface of the mounting projection.

In the present specification, the terms indicating the positional relationship in regard to the autoanalyzer, such as, upward and downward, or upper or lower, and so on, mean the positional relationship when the autoanalysis is carried out using the autoanalyzer, but do not define the positional relationship of the other states, for example, the conditions in which the autoanalyzer is delivered, or assembled. This is also applied to the present method. Further, the terms indicating the positional relationship in regard to the reaction cuvette, such as, upward and downward, or upper or lower, and so on, mean the positional relationship when the autoanalysis is carried out using the reaction cuvette in the autoanalyzer, but do not define the positional relationship of the other states, for example, the conditions, for example, before or after the cuvette is loaded on the autoanalyzer.

Effects of the Invention

The multiple autoanalyzer of the present invention has a plurality of measuring units, and thus plural measurements having different analyzing accuracies, for example, a combination of biochemical analyses and immunological analyses can be carried out in a single apparatus. Further, a measuring time can be shortened. In addition, the parts of the present apparatus are shared, and thus the apparatus becomes small-scale, and the occupation in a small space is realized. The reaction cuvette of the present invention has the arc mounting projection, and thus, a stirring operation can be smoothly carried out on the reaction base in each measuring unit.

EXPLANATION OF REFERENCE NUMBERS 1 the sample supply unit;
2 the first measuring unit;
3 the second measuring unit;
4 the reagent supply unit;
5 the third measuring unit;
5a the transporting position;
5b the additional reagent dispensing position;
5c the optical measuring position;
6 the fourth measuring unit;
7 the housing;
8 the reaction cuvette;
10 the multiple autoanalyzer;
11 the sample picking-up position;
21 the reaction base;
22 the reaction cuvette mounting zone;
25 the reaction cuvette;
25a the sample dispensing position;
25b the reagent R1 dispensing position;
25c the stirring position;
25d the reagent R2 dispensing position;
25e the optical measuring position;
25f the disposing position;
25s, 25t the cuvette-transporting position;
26 the optical measuring means;
31 the reaction base;
32 the reaction cuvette mounting zone;
35a the receiving position;
35b the reagent R3 dispensing position;
35c the stirring position;
35d the B/F separating position;
35e the cleaning position;
35f the picking-up position;
37 the optical measuring means;
41 the reagents-storing base;
42a, 42b, 42c the reagent storing lane;
43 the reagent cup;
55a the receiving position;
55b the additional reagents dispensing position;
55c the optical measuring position;
57 the optical measuring means;
81 the cuvette main part;
82 top edge of cuvette main part;
83 the picking-up projection;
83 the mounting projection;
85 the bottom of the cuvette main part;
86 the hemispherical recess;
87 the slot for the tip of a stirring rod;
87 fixing projection;
91 the stirring rod.

BEST MODE FOR CARRYING OUT THE INVENTION

Figure 1:
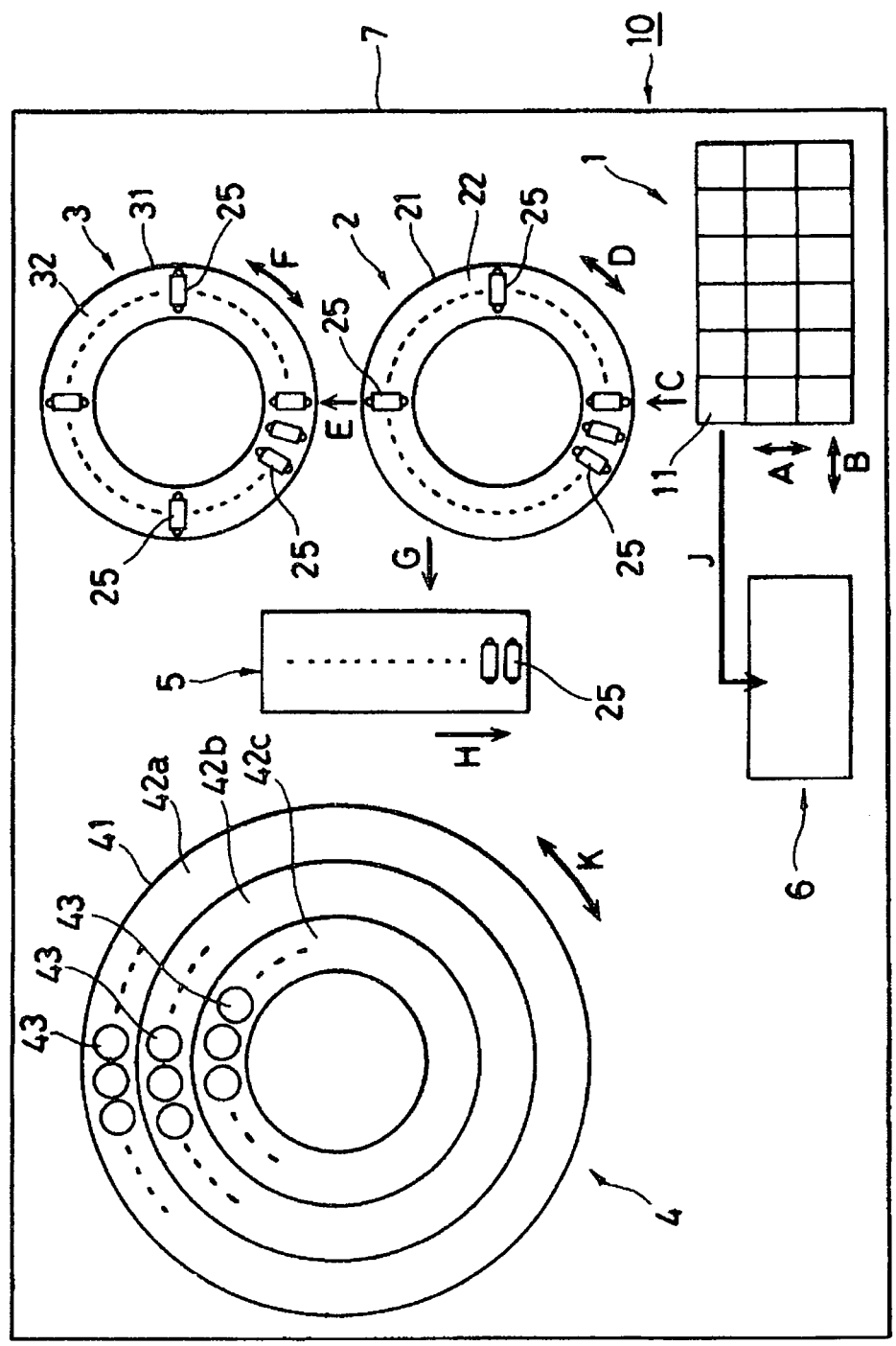
FIG. 1 is a plan view schematically illustrating a layout of units constituting the multiple autoanalyzer of the present invention.

Typical embodiments of the multiple autoanalyzer of the present invention will be explained with reference to the attached drawings. FIG. 1 is a plan view schematically illustrating a layout of units constituting the multiple autoanalyzer 10 of the present invention. As shown in FIG. 1, the multiple autoanalyzer 10 of the present invention comprises the sample supply unit 1, the first measuring unit 2, the second measuring unit 3, and the reagent supply unit 4 in the housing 7, and may further comprise the third measuring unit 5 as the additional measuring unit, and the fourth measuring unit 6 as the independent measuring unit.

The sample supply unit 1 contains a sample rack detachably holding sample cups filled with a plurality of biosamples, such as blood test samples or urine test samples. The sample supply unit 1 moves, for example, in a direction shown as an arrow A and/or arrow B, to transport pre-determined sample cups to the sample picking-up position 11, from which the reaction cuvettes on the first measuring unit 2 are then dispensed with the pre-determined biosamples by the sample-dispensing pipetter (not shown). The sample-dispensing pipetter may be, for example, a suspended pipetter hanging down from a ceiling of the housing 7 and capable of moving along a guide rail placed on the ceiling. In this case, the pipetter may be moved to a upper position above the pre-determined sample cups in the sample supply unit 1 without moving the sample supply unit 1 to take up the biosamples, and then moved to the upper position above the reaction cuvette carried on the first measuring unit 2 to dispense the cuvette therewith. Thus, the sample supply unit 1 can be fixedly placed at a predetermined position in the housing 7, and a moving means for the sample supply unit 1 is not required.

The first measuring unit 2 typically contains the reaction base 21 in the form of a rotatable table (disk), and the reaction cuvette mounting zone 22 in the form of a ring along the circumference rim of the reaction base 21. The reaction base 21 can be rotated clockwise or anticlockwise in a direction of the arrow D, and stopped at pre-determined positions, for example, the dispensing positions of samples or reagents, the stirring positions, the measuring positions, and the disposing positions. A plurality of the reaction cuvettes 25 independently from each other may be detachably held on the reaction cuvette mounting zone 22, respectively. In the illustration of FIG. 1, the number of the reaction cuvettes 25 is lessened, although many reaction cuvettes 25 are actually arranged equiangularly in a single line on the reaction cuvette mounting zone 22 with substantially very little space between adjacent reaction cuvettes 25.

The second measuring unit 3 also typically contains the reaction base 31 in the form of a rotatable table (disk), and the reaction cuvette mounting zone 32 in the form of a ring along the circumference rim of the reaction base 31. The reaction base 31 can be rotated clockwise or anticlockwise in a direction of the arrow F, and stopped at pre-determined positions, for example, the reagent-dispensing positions, the stirring positions, the measuring positions, and the disposing positions. The rotation and the stopping of the second measuring unit 3 can be synchronized with or independently from those of the first measuring unit 2. A plurality of the reaction cuvettes 25 independently from each other may be detachably held on the reaction cuvette mounting zone 32, respectively. In the illustration of FIG. 1, the number of the reaction cuvettes 25 is lessened, although many reaction cuvettes 25 are actually arranged equiangularly in a single line on the reaction cuvette mounting zone 32 with substantially very little space between adjacent reaction cuvettes 25.

The reagent supply unit 4 typically contains the reagents-storing base 41 in the form of a rotatable table (disk), and a plurality of the concentric-ring reagents-storing lanes 42a, 42b, 42c on the reagents-storing base 41. In each of the reagent storing lanes 42a, 42b, 42c, are placed the reagent cups 43 storing various reagents necessary for the measurements in the measuring units, for example, the first measuring unit 2, the second measuring unit 3, and optionally, the third measuring unit 5 as the additional unit, in the multiple autoanalyzer of the present invention. The reagents-storing base 41 can be rotated clockwise or anticlockwise in a direction of the arrow K, and stopped at pre-determined positions, for example, the positions for taking up the reagents, or the positions for taking or removing the reagent cups. In the illustration of FIG. 1, the number of the reagent cups 43 is lessened, although many reagent cups 43 are actually arranged equiangularly in a single line on each of the concentric-ring reagents-storing lanes 42a, 42b, 42c with substantially very little space between adjacent reagent cups 43.

The reagents-storing base 41 in the form of a rotatable table may have a structure wherein a single table rotates as a whole, or have a multiple-rings structure wherein plural concentric-ring reagents-storing lanes, for example, the reagent storing lanes 42a, 42b, 42c, rotate independently of each other. In the case of the multiple-rings structure wherein plural concentric-ring reagents-storing lanes rotate independently of each other, each ring can be rotated clockwise or anticlockwise or stopped independently from each other, whereby reagents can be effectively supplied to each measuring unit independently from each other.

Figure 2:
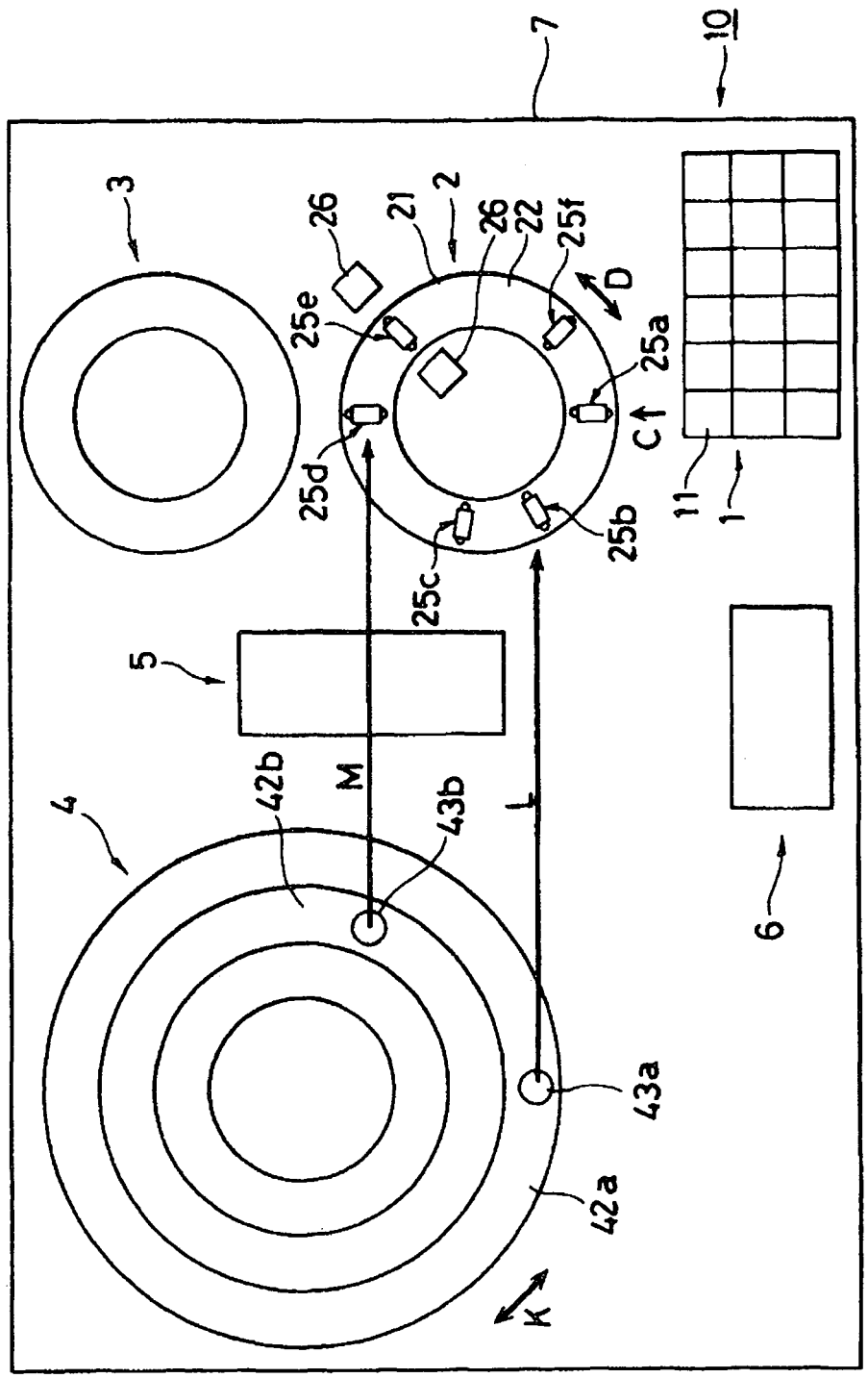
FIG. 2 is a schematical view illustrating the measuring procedure in the first measuring unit.

Then, the case wherein the measurements of biochemical items and latex agglutination are carried out in the first measuring unit 2, using a colorimetric or nephelometric measurement, will be explained hereinafter, referring to FIG. 2. An empty reaction cuvette 25 carried on the reaction cuvette mounting zone 22 of the reaction base 21 in the first measuring unit 2 is stopped at the sample dispensing position 25a, and dispensed with the biosample in the pre-determined sample cup 11 in the sample supply unit 1 by the sample-dispensing pipetter (not shown). Reference is made to the arrow C in FIGS. 1 and 2. Then, the reaction cuvette 25 is moved to the position 25b for the dispensing with the reagent R1 by the rotation of the reaction base 21 and stopped thereat, at which it is dispensed with the reagent R1 from the reagent supply unit 4 (see the arrow L in FIG. 2). The dispensing with the reagent R1 may be conducted by, for example, a suspended reagents-dispensing pipetter (not shown) hanging down from a ceiling of the housing 7 and capable of moving along a guide rail placed on the ceiling. The suspended reagents-dispensing pipetter may be moved to the upper position above, for example, the pre-determined reagent cup 43a on the reagent storing lane 42a in the reagent supply unit 4 to take up the reagent R1, and then moved to the upper position above the reaction cuvette 25 carried on the reagent R1 dispensing position 25b on the first measuring unit 2 to dispense the reaction cuvette 25 therewith.

Then, the reaction cuvette 25 dispensed with the biosample and the reagent R1 is moved to the stirring position 25c by the rotation of the reaction base 21, and stopped and stirred thereat. Thereafter, the reaction cuvette 25 is moved to the reagent R2 dispensing position 25d by the rotation of the reaction base 21, stopped thereat, and then, dispensed with the reagent R2 from the reagent supply unit 4 (see the arrow M in FIG. 2). The dispensing with the reagent R2 may be conducted by a suspended reagents-dispensing pipetter (not shown) as above. The suspended reagents-dispensing pipetter may be moved to the upper position above, for example, the pre-determined reagent cup 43b on the reagent storing lane 42b in the reagent supply unit 4 to take up the reagent R2, and then moved to the upper position above the reaction cuvette 25 carried on the reagent R2 dispensing position 25d on the first measuring unit 2 to dispense the reaction cuvette 25 therewith.

Then, the reaction cuvette 25 dispensed with the reagents R1 and R2 is moved to the stirring position 25c by the rotation of the reaction base 21, and stopped thereat and stirred again. The position for the second stirring may be set at a different position. Thereafter, the reaction cuvette 25 is moved by the rotation of the reaction base 21 to pass the optical measuring position 25e. During the passage, the change caused by the reaction in the reaction cuvette is measured by the optical measuring means 26 capable of measurement by the transmitted or scattered light or the like. When the optical measuring is conducted, the reaction cuvette 25 may be stopped at the optical measuring position 25e. Thereafter, the reaction cuvette 25 is moved eventually up to the disposing position 25f and stopped to be removed from the reaction base 21 to the disposing chamber (not shown) by a picking-up means (not shown).

Figure 3:
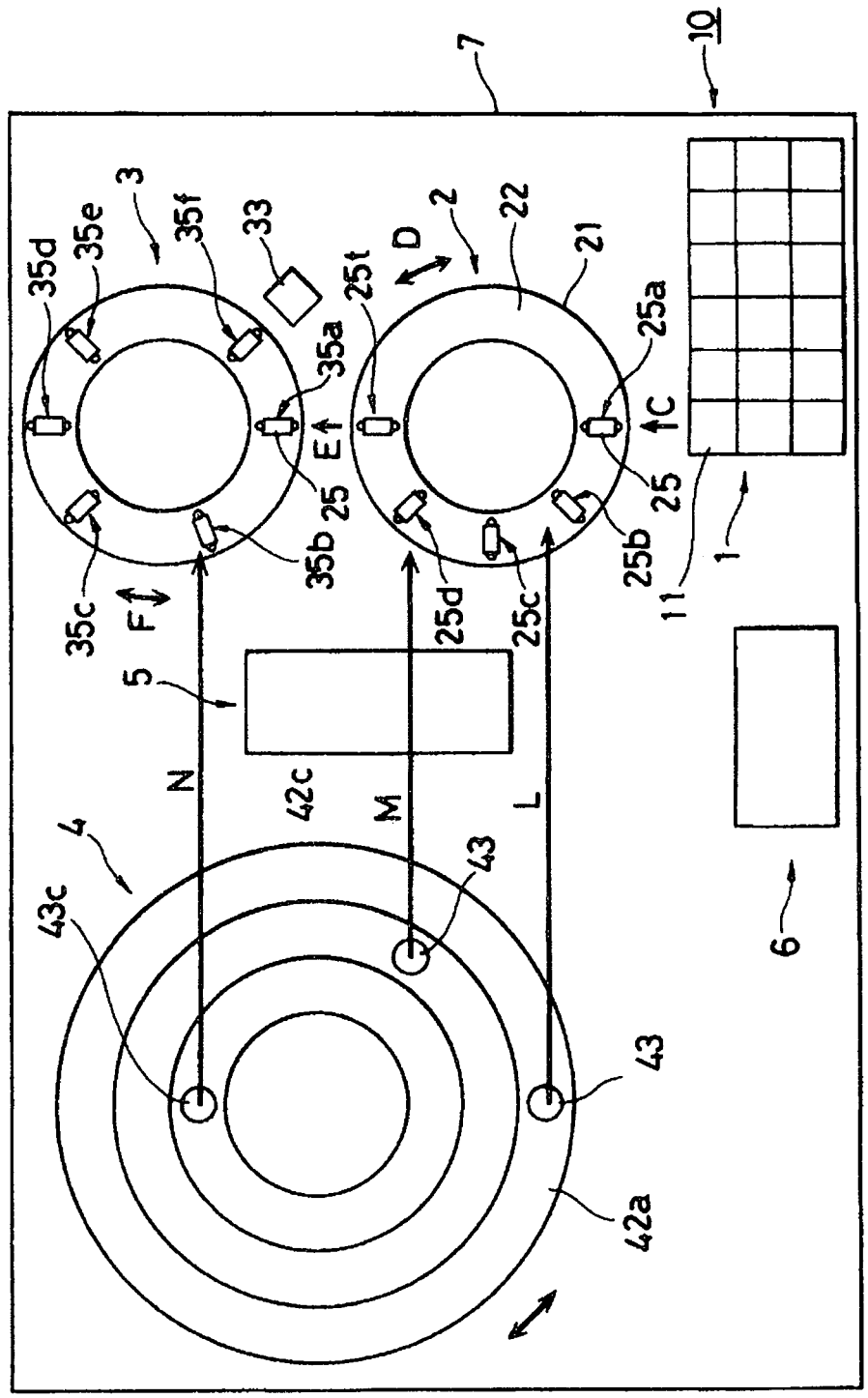
FIG. 3 is a schematical view illustrating the measuring procedure in the second measuring unit.

Then, the case wherein the measurements of an enzyme immunoassay are carried out in the second measuring unit 3, using chemiluminescence, will be explained hereinafter, referring to FIG. 3. When the measurements are carried out in the second measuring unit 3, the sample-dispensing and a part of the reagents-dispensing (or only the sample-dispensing) are carried out on the reaction base 21 of the first measuring unit 2. Specifically, first, an empty reaction cuvette 25 carried on the reaction cuvette mounting zone 22 of the reaction base 21 in the first measuring unit 2 is stopped at the sample dispensing position 25a, and dispensed with the biosample in the pre-determined sample cup 11 in the sample supply unit 1 by the sample-dispensing pipetter (not shown), as above. Reference is made to the arrow C in FIG. 3. Then, the reaction cuvette 25 is moved to the position 25b for the dispensing with the reagent R1 by the rotation of the reaction base 21 and stopped thereat, at which it is dispensed with the reagent R1 from the reagent supply unit 4 by, for example, the suspended reagents-dispensing pipetter (not shown). Reference is made to the arrow L in FIG. 3.

As above, the reaction cuvette 25 dispensed with the biosample and the reagent R1 is moved to the stirring position 25c, and stopped thereat and stirred. Thereafter, the reaction cuvette 25 is moved to the reagent R2 dispensing position 25d, stopped thereat, and then, dispensed with the reagent R2 from the reagent supply unit 4 (see the arrow M in FIG. 3). Subsequently, the reaction cuvette 25 is moved to the cuvette-transporting position 25t and stopped thereat, after being stirred at the stirring position 25c, if necessary.

At the cuvette-transporting position 25t, the reaction cuvette 25 is picked up by the picking-up means (not shown) from the reaction base 21, and transferred to the receiving position 35a on the reaction base 31 of the second measuring unit 3 (see the arrow E). Thereafter, the reaction cuvette 25 is moved to the reagent R3 dispensing position 35b by the rotation of the reaction base 31 (see the arrow F), stopped thereat, and then, dispensed with the reagent R3 from the reagent supply unit 4, if necessary (see the arrow N in FIG. 3). The dispensing with the reagent R3 may be conducted by a suspended reagents-dispensing pipetter (not shown). The suspended reagents-dispensing pipetter may be moved to the upper position above, for example, the pre-determined reagent cup 43c on the reagent storing lane 42c in the reagent supply unit 4 to take up the reagent R3, and then moved to the upper position above the reaction cuvette 25 carried on the reagent R3 dispensing position 35b on the second measuring unit 3 to dispense the reaction cuvette 25 therewith. If the dispensing with the reagent R3 is not necessary, the above procedure is omitted. The dispensing with the reagent R2 can be conducted at the reagent R3 dispensing position 35b, without dispensing the cuvette with the reagent R2 at the first measuring unit 2.

The reaction cuvette 25 dispensed with the reagent R3 (or the reagent R2) is moved to the stirring position 35c by the rotation of the reaction base 31, and stopped thereat and stirred. Then, the reaction cuvette 25 is subjected to the B/F separation. When magnetic beads are used, the B/F separation can be carried out by a magnet. When a magnet is used, it takes a longer time to collect the magnetic beads, and thus, the stopping time at the reaction base 31 becomes relatively longer. In the present apparatus, however, the reaction base 31 of the second measuring unit 3 is separated from the reaction base 21 of the first measuring unit 2, and the case that a long stopping time of the rotation prolongs the whole treating time can be prevented.

After the B/F separation, the reaction cuvette 25 is moved to the cleaning position 35e, and stopped thereat and washed. Then, the reaction cuvette 25 is moved to the picking-up position 35f and stopped thereat, and transferred to the optical measuring means 33 by a suitable picking-up means (not shown). The optical measuring means 33 is, for example, a means capable of measuring the change based on the reaction in the reaction cuvette by chemiluminescence. The above optical measurement can be conducted on the reaction base 31. If the above optical measurement is conducted on the reaction base 31, the measurement can be carried out while the reaction cuvette 25 passes through the optical measuring position (not shown), or by stopping the reaction cuvette 25 at the optical measuring position (not shown). After the measurement, the reaction cuvette 25 is removed from the optical measuring means 33 to the disposing chamber (not shown).

The multiple autoanalyzer of the present invention can contain one or more additional measuring units in addition to the above first measuring unit 2 and second measuring unit 3. The additional measuring unit may be an embodiment (pre-supplying type) wherein the reaction cuvette is received from the first measuring unit 1 by a suitable cuvette-transferring means after being dispensed with the biosamples and optionally a part of the reagents on the first measuring unit 1, or an embodiment (directly supplying type) wherein the biosamples are supplied directly from the sample supply unit 1. Further, the additional measuring unit may be an additional reagent-demanding type which necessitates a supplement of an additional reagent from the reagent supply unit 4, or an additional reagent-free type which does not require an additional reagent from the reagent supply unit 4.

The multiple autoanalyzer of the present invention can contain one or more independent measuring units in addition to the above first measuring unit 2 and the above second measuring unit 3, and in addition to or instead of the above one or more additional measuring units. In the independent measuring unit, the biosamples are supplied directly from the sample supply unit 1, and the measurements can be conducted without a supply of the reagents from the reagent supply unit 4. The independent measuring unit is, for example, a unit for measuring body fluid electrolytes.

Figure 4:
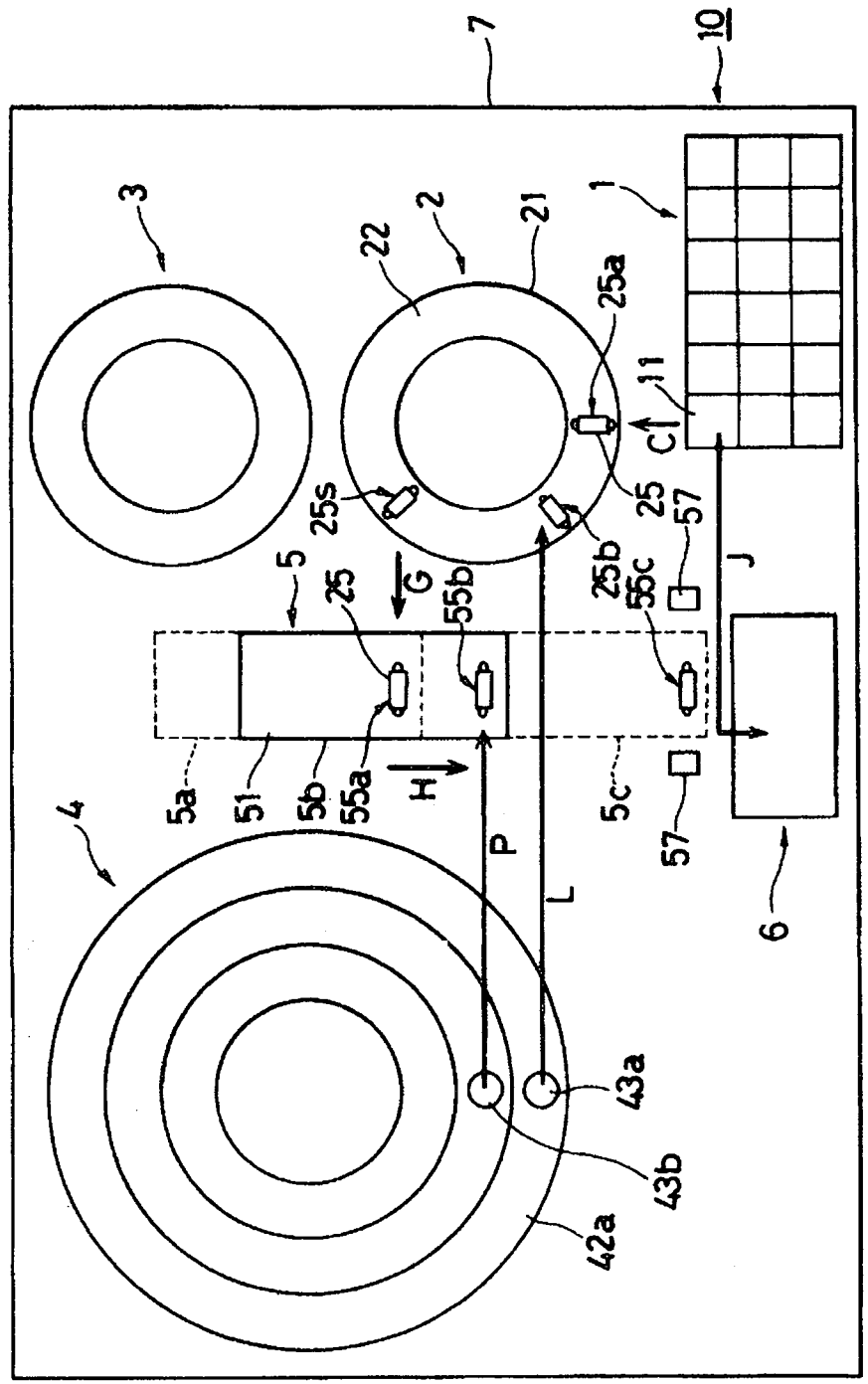
FIG. 4 is a schematical view illustrating the measuring procedures in the third and fourth measuring unit.

Referring to FIG. 4, an embodiment equipped with the third measuring unit 5 which is the pre-supplying type, and at the same time, the additional reagent-demanding type, as the additional measuring unit, and with the fourth measuring unit 6 as the independent measuring unit will be explained hereinafter. In the third measuring unit 5 which is the pre-supplying type, and at the same time, the additional reagent-demanding type, for example, a blood coagulation time measurement can be carried out in addition to the measurements in the first measuring unit 2 and the second measuring unit 3. When the measurement is conducted in the third measuring unit 5 as the pre-supplying type, the dispensing with the samples and a part of the reagents is carried out on the reaction base 21 of the first measuring unit 2. Specifically, first, an empty reaction cuvette 25 carried on the reaction cuvette mounting zone 22 of the reaction base 21 in the first measuring unit 2 is stopped at the sample dispensing position 25a, and dispensed with the biosample from the sample supply unit 1 by the sample-dispensing pipetter (not shown), as above. Reference is made to the arrow C in FIG. 4. Then, the reaction cuvette 25 is moved to the position 25b for the dispensing with the reagent R1 and stopped thereat and it is dispensed with the reagent R1 from the reagent supply unit 4 by, for example, the suspended reagents-dispensing pipetter (not shown). In the first measuring unit 2, only the dispensing with the sample can be conducted, without the dispensing with the reagent.

Thereafter, after being stirred and dispensed with the reagent R2 as above, if necessary, the reaction cuvette 25 is moved to the cuvette-transporting position 25s and stopped. At the cuvette-transporting position 25s, the reaction cuvette 25 is picked up by the picking-up means (not shown) from the reaction base 21, and transported to the receiving position 55a (see the arrow G) on the reaction base 51 of the third measuring unit 5 at the receiving position 55a (shown by a broken line in FIG. 4). The third measuring unit 5 may be a unit containing a reaction base in the form of a circular rotatable table as the first measuring unit 2 and the second measuring unit 3, or a unit containing a reaction base in the form of a rectangular table capable of linearly reciprocating in the direction shown by the arrow H, or in the opposite direction.

After receiving the reaction cuvette 25 at the transporting position 5a, the third measuring unit 5 is moved to the additional reagent dispensing position 5b (shown by the solid line in FIG. 4) by the linear sliding movement of the reaction base 51 (in the direction of the arrow H) and stopped thereat. At the additional reagents dispensing position 55b, the cuvette 25 is dispensed with an additional reagent from the reagent supply unit 4, by, for example, the suspended reagents-dispensing pipetter (not shown), as shown by the arrow P. Further, the optical measuring means (not shown) are placed at the positions where the reaction cuvettes 25 are mounted on the reaction base 51. For example, the optical measuring means composed of a transmitter and receiver for measuring a transmitted light are placed at both sides of the position mounting the reaction cuvette 25, and a measurement of a transmitted light can be conducted at an interval of 0.1 second. Instead of placing the optical measuring means on the reaction base 51, for example as shown in FIG. 4, the third measuring unit 5 is moved to the optical measuring position 5c shown by a broken line in FIG. 4 by the linear sliding movement of the reaction base 51 in the direction of the arrow H and stopped thereat, and the change based on the reaction in the reaction cuvette can be measured by, for example, the optical measuring means 57 through a transmitted light, at the optical measuring position 5c. After the measurement, the reaction cuvette is moved to and stopped at the disposing position (not shown), and removed from the reaction base 51 by the picking-up means (not shown) to the disposing chamber (not shown).

The biosample is supplied directly from the sample supply unit 1 to the fourth measuring unit 6 as the independent measuring unit, by the sample-dispensing pipetter (not shown), as shown by the arrow J in FIG. 4. The fourth measuring unit 6 may be, for example, a unit for measuring body fluid electrolytes, particularly, an ion detector equipped with various ion-selective electrodes. The ion-selective electrode may be, for example, a halogen-ion-selective electrode, or an alkali-metal-ion-selective electrode.

In the multiple autoanalyzer of the present invention, the installation positions and orders (neighboring relationships) of the first measuring unit and the second measuring unit, and one or more additional measuring units optionally contained, as well as the kinds of measuring items and the kinds of optical measuring means therein, are not limited, so long as the samples are supplied commonly from the sample supply unit in the first measuring unit.

In the multiple autoanalyzer of the present invention, it is preferable to locate the first measuring unit at the adjacent position very close to the sample supply unit, because a plurality of the reaction cuvettes independently from each other are dispensed with the samples from the sample supply unit intensively only in the first measuring unit. If the sample supply unit and the first measuring unit are close to each other, a movement of transporting the samples for dispensing becomes simple and shortened, and thus, the dispensing time can be shortened and the apparatus structure can be simplified. In comparison with the conventional apparatus wherein the dispensing with samples is separately conducted in each measuring unit, respectively, the cuvettes are dispensed with samples intensively only in the first measuring unit, and merely transferred to the second measuring unit and the additional measuring units (the third measuring unit or the like) in the multiple autoanalyzer of the present invention. Therefore, a total treatment time including the dispensing time can be shortened and the mechanism can be simplified.

In the first measuring unit, for example, a biochemical or immunological measurement can be carried out. The substances of the biochemical measurement may be those to be examined in a conventional biochemical clinical assay, for example, various enzymes, sugars, lipids, plasma (serum) proteins, nonprotein nitrogen compounds, biocolorants, tumor markers. The immunological measurements may be those using transmitted or scattered light, for example, immuno-nephelometry or latex agglutination, and the subjects to be examined may be, for example, D-dimmer, FDP, or HCV.

The second measuring unit is different from other measuring units, and thus, for example, a measurement with a high accuracy can be conducted. In the measurement with a high sensitivity, a reaction of substances having a specific affinity may be particularly used. The reaction of substances having a specific affinity may be, for example, an antigen-antibody reaction, a reaction of nucleic acids (DNA or RNA), or a reaction of a receptor and a legend.

In the reaction of substances having a specific affinity, an amount of substances bound to the above substances having a specific affinity is measured. The reaction can be classified generally to a homogeneous method wherein, when the substance with a specific affinity is bound with the substance to be bound thereto, a change is caused in the substance per se bound to the substance with a specific affinity or in a tracer attached to the substance bound to the substance with specific affinity, and thus, a mass of the substance bound to the substance with a specific affinity is measured, and a heterogeneous method wherein, after a complex of the substance with a specific affinity and the substance to be bound thereto is made insoluble, a B/F separation is required to separate the substance bound to the substance with a specific affinity and the substance not bound to the substance with a specific affinity. In the present invention, either of a homogeneous method and a heterogeneous method can be conducted in the second measuring unit. A method using a radioactive isotope as a tracer, or an enzyme immunoassay (EIA) using an enzyme as a tracer can be used.

In the second measuring unit, for example, FIA, EIA, or CLEIA can be carried out. The subjects to be examined may be, for example, CEA, CA19-9, T3, T4, FT3, FT4, HBsAg, TAT, or TSH.

In the third measuring unit, for example, a measurement of a blood coagulation time or a measurement of the activity using a synthetic substrate can be conducted. The blood coagulation time measurement may be, for example, a measurement of protobine time, activated partially activated thromboplastine time, or fibrinogen. In the fourth measuring unit, for example, a measurement of electrolytes can be conducted. The substances for the measurement of electrolytes may be, for example, Na ion, K ion, or chloride ion.

In the first measuring unit, it is preferable to conduct a measurement using transmitted or scattered light, for example, a colorimetric or turbidimetric measurement. In the second measuring unit, it is preferable to conduct a measurement using chemiluminescence or fluorescence, for example, CLEIA. In the third measuring unit, it is preferable to conduct a measurement using transmitted or scattered light, for example, in a measurement of blood coagulation time. In the fourth measuring unit, it is preferable to conduct a measurement using an electromotive force, for example, a method using ion-selective electrodes.

In the multiple autoanalyzer of the present invention, it is preferable to conduct a combination of a biochemical or latex agglutination measurement by a colorimetric or nephelometric measurement in the first measuring unit, an enzyme immunoassay by chemiluminescence in the second measuring unit, and a measurement of blood coagulation time in the third measuring unit. Further, it is preferable to conduct an ion analysis in the fourth measuring unit in addition to the above combination. In the second measuring unit as above, a magnetic carrier is preferably used in the enzyme immunoassay by chemiluminescence. In this case, the B/F separation can be conducted by a conventional technique using a magnet.

In the multiple autoanalyzer of the present invention, it is preferable that the first optical measuring means in the first measuring unit, the second optical measuring means in the second measuring unit, and the third optical measuring means in the third measuring unit as the additional measuring unit be optical detectors different from each other. As each of the first optical measuring means, the second optical measuring means, and the third optical measuring means, for example, (1) an optical detector containing a light emission diode and a diode array, (2) an optical detector containing a lamp unit and a spectrometer or (3) an optical detector containing a photomultiplier as a photodetector may be used.

The optical detector containing a light emission diode and a diode array may be used, for example, in a measurement of a blood coagulation time; the optical detector containing a lamp unit and a spectrometer may be used, for example, in a colorimetric or turbidimetric measurement; and the optical detector containing a photomultiplier as a photodetector may be used, for example, a measurement of chemiluminescence.

In the multiple autoanalyzer of the present invention, it is preferable that each of the measurement units or at least one of the measurement units contains a means for detecting an abnormal sample. The abnormal sample means a sample containing an extremely high concentration of the substance to be examined; sometimes such a high concentration cannot be detected. An abnormal sample contains non-specific analytes (analytes agglomerating magnetic latex). Such abnormal samples can be detected, for example, by an absorbance change.

Figure 5:
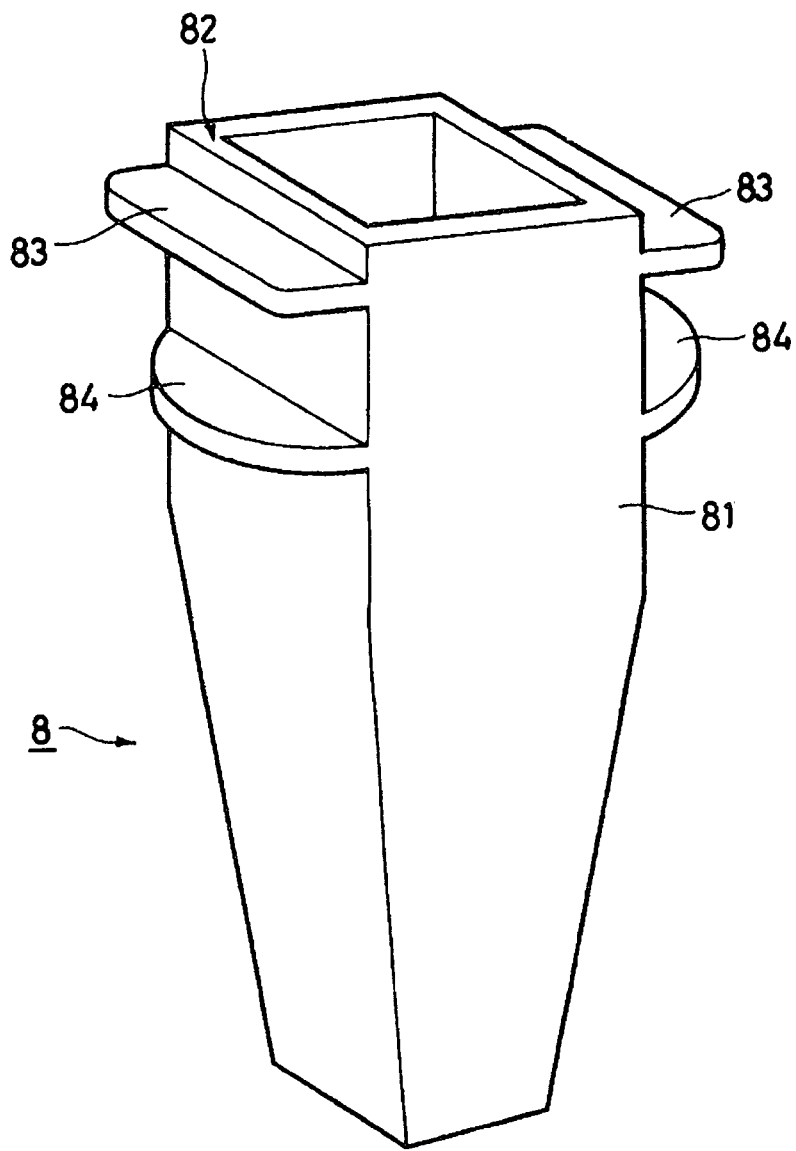
FIG. 5 is a perspective view of the reaction cuvette of the present invention.
Figure 6:
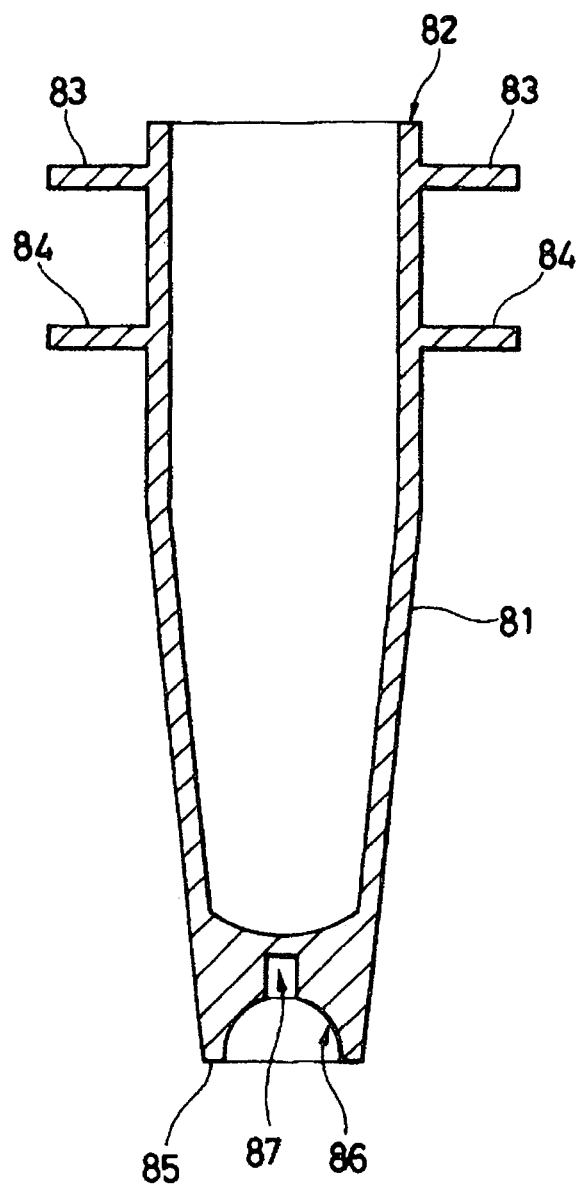
FIG. 6 is a sectional view of the reaction cuvette of FIG. 5.
Figure 7:
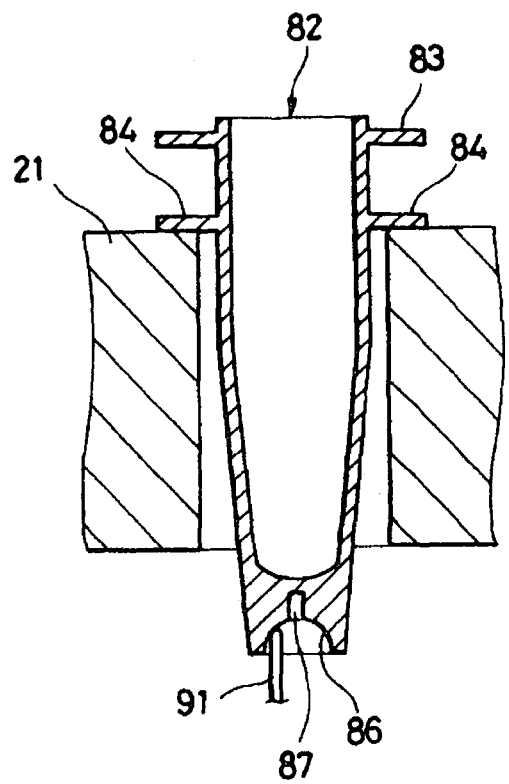
FIG. 7 is a sectional view of the reaction cuvette of FIG. 5 when it is mounted on the reaction base.

The present invention also relates to the reaction cuvette. Typical embodiments of the reaction cuvette according to the present invention will be explained with reference to FIGS. 5 to 8. FIG. 5 is a perspective view of the reaction cuvette 8 of the present invention, and FIG. 6 is a sectional view thereof. FIG. 7 is a schematical sectional view of the reaction cuvette, for example, in the state that it is mounted on the reaction base 21 of the first measuring unit 2 in the multiple autoanalyzer as shown in FIGS. 1 to 4, and FIG. 8 is a schematical sectional view of the reaction cuvette in the state that it is inclined by the stirring rod.

The reaction cuvette 8 of the present invention contains a pair of picking-up projections 83, 83 at the top edge 82 of the cuvette main part 81 in the form of a generally rectangular parallelepiped, and a pair of the mounting projections 84, 84 under the picking-up projections. The reaction cuvette 8 can be mounted on the reaction base of the measuring units by inserting the lower portion of the cuvette main part 81 into a mounting through-hole or a mounting recess or groove bored in the reaction base. The picking-up projection 83 is used as a holding part for the picking-up means, for example, when the reaction cuvette mounted on the reaction base 21 of the first measuring unit 2 in the multiple autoanalyzer as shown in FIGS. 1 to 4 is picked up and transferred to the reaction base 31 of the second measuring unit 3. Therefore, it is necessary to locate the picking-up projection 83 at the position protruding upward from the surface of the reaction base so that the picking-up means can hold the picking-up projection 8 when the reaction cuvette 83 is mounted on the reaction base of the measuring units.

The mounting projection 84 is placed on the upper portion of the cuvette main part 81, and has a catch function to be brought into contact with the surface of the reaction base 21 (or the reaction base 31) and is prevented from falling, when the cuvette main part 81 is mounted on the reaction base in the multiple autoanalyzer as shown in FIGS. 1 to 4, by inserting the reaction cuvette into the mounting through-hole or the mounting recess or groove bored in the reaction base 21 of the first measuring unit 2 (or the reaction base 31 of the second measuring unit 3). Further, the reaction cuvette 8 of the present invention contains the hemispherical recess 86 on the bottom 85 of the cuvette main part 81 and a slot 87 into which the tip of a stirring rod 91 can be inserted, at the center of the recess 86.

Figure 8:
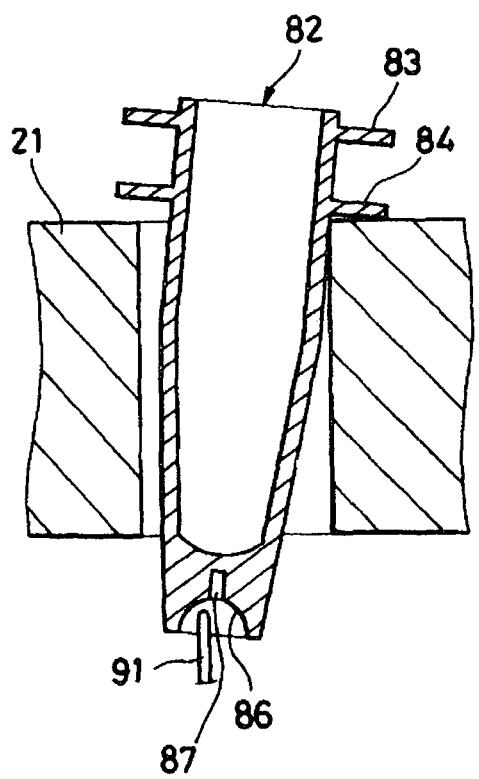
FIG. 8 is a sectional view of the reaction cuvette of FIG. 5 when it is mounted on the reaction base, and a stirring procedure started.

As shown in FIGS. 7 and 8, after the reaction cuvette 8 of the present invention having the above structure is inserted into the mounting through-hole in the reaction base 21 and mounted thereon, and then moved to and stopped at the stirring position, the tip of the stirring rod 91 of a stirring device (not shown) is inserted into the hemispherical recess 86. As shown in FIG. 7, the hemispherical recess 86 is deflected from the center to the circumferential rim so that the tip of the stirring rod 91 is not inserted to the center of the bottom face 85 of the reaction cuvette 8. The stirring rod 91 is inserted defectively into the hemispherical recess 86, and thus, the tip comes into contact with a wall surface of the hemispherical recess 86. Therefore, as shown in FIG. 8, the reaction cuvette 8 is inclined on the reaction base 21. However, the tip of the stirring rod 91 further pushes up the hemispherical recess 86, and eventually is inserted into the slot 87.

The stirring of the reaction cuvette 8 starts when the tip of the stirring rod 91 comes into contact with the wall surface of the hemispherical recess 86. If the mounting projection 84 is a rectangular plate, the contact with the surface of the reaction base 21 becomes irregular, and thus, the reaction cuvette 8 cannot be smoothly stirred. In the reaction cuvette 8 of the present invention, however, the tip of the mounting projection 84 has an arc form, so that the contact with the surface of the reaction base 21 does not become irregular, and the reaction cuvette 8 is smoothly stirred. Therefore, the reaction cuvette of the present invention can be effectively used in an autoanalyzer with a stirring treatment.

The recess provided on the bottom face of the reaction cuvette of the present invention has a rounded wall surface. Preferably, the rounded wall surface has a shape such that the tip of the stirring rod is eventually guided smoothly to the center of the recess in the course of the stirring treatment, although it has first come into contact with the wall surface of the peripheral portion of the recess. Therefore, the rounded wall surface may be, for example, hemispherical as shown in FIGS. 6 to 8, or of elliptic hemispherical, circular conical, or truncated conical. When the rounded wall has a hemispherical or elliptic hemispherical surface, it is preferable to place the slot for the tip of a stirring rod at the center of the recess. When the rounded wall has a truncated conical surface, it is preferable to place the slot for the tip of a stirring rod at the center of the truncated portion. Further, when the rounded wall has a circular conical surface, the top of the cone serves as the slot for the tip of the stirring rod.

The reaction cuvette of the present invention can be stirred by an action from the outside as above, without inserting the stirring rod into the sample, and thus is preferably used in the case wherein the measuring items contain a coagulation time measurement. If a sample of the coagulation time measurement is stirred by inserting the stirring rod thereinto, a coagulation system is influenced and the measurement results may be inaccurate.

Preferably, the reaction cuvette of the present invention has four parallel flat side walls of the cuvette main part in the form of a generally rectangular parallelepiped so that measurements using transmitted light, such as biochemical measuring items or measurements in LPIA using turbidity can be favorably carried out. Further, the reaction cuvette of the present invention preferably has a rounded portion (hemispherical or elliptic hemispherical bottom face) on the inner bottom. If it does not have a rounded portion on the inner bottom, the liquid is drawn up along the inner wall of the cuvette by a capillary action, and thus, washing may be insufficient. Particularly, when chemiluminescence with a high sensitivity is measured, for example, an antibody labeled with alkaline phosphatase or the like may remain and thus cause an error in the measurement.

Figure 9:
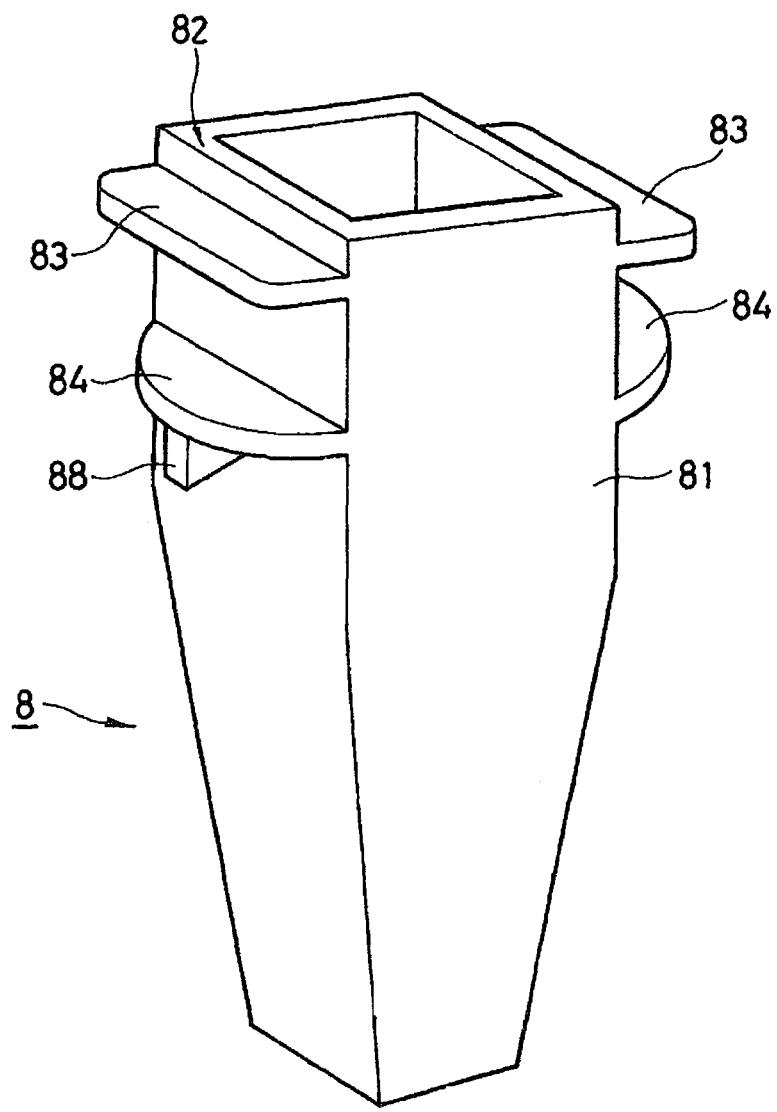
FIG. 9 is a perspective view of the reaction cuvette having a fixing projection.
Figure 10:
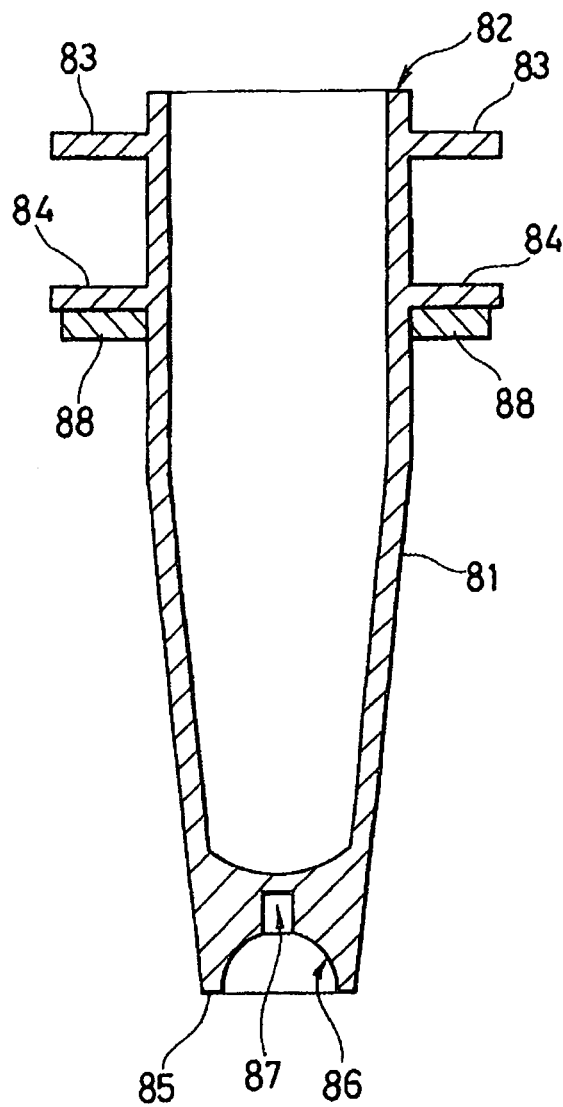
FIG. 10 is a sectional view of the reaction cuvette of FIG. 9.
Figure 11:
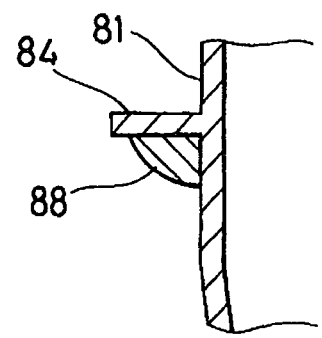
FIG. 11 is a sectional view of another embodiment of the reaction cuvette having a fixing projection.

As shown in FIGS. 9 and 10, the reaction cuvette of the present invention can contain the fixing projections 88, 88 on one or both of undersurfaces of a pair of the mounting projections 84, 84. The fixing projection 88 is a projected plate protruding downward from the undersurface of the mounting projection 84. As shown in FIG. 11 (partial sectional view), it may have a rounded surface on the outside edge opposite to the cuvette main part. When the reaction cuvette having the fixing projection is used, the recess or groove is fitted at the edge of the mounting through-hole on the surface of the reaction base carrying such a reaction cuvette so that the fixing projection 88 can be inserted into the recess or groove, and the lower portion of the cuvette main part 81 can be inserted into the mounting through-hole. As above, the cuvette can be fixed and positioned more firmly, by providing the fixing projection 88 on one or both of undersurfaces of the mounting projections 84, 84 of the reaction cuvette, and at the same time, providing the recess or groove for the fixing projection 88 on the surface of the reaction base.

The preferable embodiments of the present apparatus are as follows: The preferable embodiment of the present apparatus has at least three detecting systems which are different from each other. Further, as mentioned above, the optical systems of the first measuring unit, the second measuring unit and the third measuring unit are different from each other. The optical systems are composed of different detecting systems, for example, (1) a unit using transmitted or scattered light (a detecting apparatus containing a lamp unit and a spectrometer, (2) a unit with a high sensitivity (an optical detector containing a photomultiplier as a photodetector in the case of chemiluminescence), and (3) a unit for detecting coagulation time (a detecting apparatus containing LED and a diode array).

In order to realize the above structure, the apparatus must have a mechanism capable of loading cuvettes independently from each other. In almost all of the conventional autoanalyzers, plural reaction cuvettes are loaded in a combined state, the reaction and detection are carried out, and then the reaction liquid is removed with suction, washed with washing liquid, and reused. In the present apparatus, however, for example, when the sample A is examined for immunonephelometry, chemiluminescence and coagulation time, and the sample B is examined for chemiluminescence and coagulation time, three cuvettes are dispensed with the sample A and two cuvettes are dispensed with the sample B on a particular measuring unit. Each of cuvettes necessary for each detecting system is stirred, and picked up at particular positions, and transported to each measuring unit. Although not shown in Figures, the cuvettes are picked up by arms of the apparatus and inserted into cuvette holes at particular positions for subsequent steps. Further, each of detections proceeds independently and in parallel, and the measurements can be effectively conducted.

In the present apparatus, fresh cuvettes are automatically and continuously loaded to particular positions of particular measuring units. In each of the measuring units, compositions (contents) of the reagents supplied to the cuvettes actually vary with measuring systems. In order to effectively supply various reagents, for example, plural rings are concentrically combined on a single reagent table region, whereby each ring can be driven separately, and many kinds of reagents can be stored. The plural concentric rings have different distances from the center. Thus, the distance differences can be used to drive syringes for dispensing the cuvettes placed on the measuring units with the reagents in a linear movement, whereby the apparatus can be minimized, and the driving can be simplified to lessen errors.

As above, all of the cuvettes have a structure capable of being necessarily stirred, in the mid-course (for example, after mixing a sample and a reagent) at any measuring units. The present apparatus contains, for example, the measuring unit for a blood coagulation time, and thus, the stirring mechanism of the present apparatus is very favorable, because, if a sample is stirred by a probe (a stirring fin), the probe is unfavorably wound around with fibrin masses. The structure of the present cuvette is very important for effectively stirring individual cuvettes independently from each other. Specifically, the cuvette has wings (the mounting projections) and it can be stirred in a slightly inclined state. Further, it is preferable to contain the fixing projection so as to easily fix the cuvette into the cuvette hole and position the cuvette more firmly. As the shape of the cuvette is a rectangular parallelepiped, the distance of the transmitted light can be strictly fixed to inhibit a dispersion of the measurement results.

Therefore, the shape of the present cuvette is preferable, because the cuvettes must be independent from each other in the measuring unit composed of plural different detecting systems as in the present invention, and the stirring effect can be enhanced. As above, the apparatus composed by integrating three or more different detecting systems into a single apparatus did not exist until now. In comparison with the combination of different apparatuses for different detecting systems, the present apparatus is advantageous in that measured results from plural different detecting systems can be obtained all together. In the prior art, individual results are shown in the measuring apparatuses, respectively.

INDUSTRIAL APPLICABILITY

The multiple autoanalyzer of the present invention can measure plural kinds of analyses with different measuring accuracies, such as biochemical analyses and immunological analyses, by a single apparatus. The reaction cuvette of the present invention can effectively be used in an autoanalyzer wherein a stirring procedure is carried out. As above, the present invention was explained with reference to particular embodiments, but modifications and improvements obvious to those skilled in the art are included in the scope of the present invention.

The invention claimed is:

1. A reaction cuvette having:
a main part comprising parallel flat side walls,
a rounded portion of an inner bottom,
a recess with a rounded wall surface extending into an outer bottom face of the main part toward the inner bottom, and
a slot extending from the center of the recess and further towards the inner bottom than the recess, the slot configured to receive a tip of a stirring rod,
wherein the rounded portion has a hemispherical or elliptic hemispherical bottom face, and
wherein the rounded wall surface is hemispherical, elliptical hemispherical, circular conical, or truncated conical.

2. The reaction cuvette according to claim 1, further having a mounting projection protruding from an upper sidewall of the cuvette main part, the mounting projection having an arc-shaped form.

3. The reaction cuvette according to claim 2, further comprising a fixing projection protruding downward from an undersurface of the mounting projection.

4. The reaction cuvette according to claim 1, wherein the parallel flat side walls of the main part of the cuvette comprise four parallel flat side walls.

5. The reaction cuvette according claim 1, wherein the slot does not extend through the main part.

6. The reaction cuvette according claim 1, wherein the center of the recess is the furthest portion of the recesses towards the inner bottom.

7. A combination comprising the reaction cuvette according to claim 1 and a stirring device.

8. An apparatus for a multiple automatic analysis of biosamples comprising
a sample supply unit configured to hold a plurality of biosamples;
a first measuring unit fitted with a first optical measuring means, said first measuring unit being capable of detachably holding, in mutually independent manner, a plurality of reaction cuvettes independent from each other;
a sample transport means capable of transporting the biosamples from the sample supply unit to one of the plurality of reaction cuvettes on the first measuring unit;
a second measuring unit fitted with a second optical measuring means, said second measuring unit being capable of receiving a reaction cuvette transferred from the first measuring unit and detachably holding, in a mutually independent manner, a plurality of reaction cuvettes independent from each other;
a reagent supply unit configured to hold reagents for use in a measurement by the first measuring unit and in a measurement by the second measuring unit; and
a reagent transport means capable of transporting reaction reagents, in a mutually independent manner, from the reagent supply unit to one of the plurality of reaction cuvettes on at least one of the first measuring unit and the second measuring unit,
wherein the plurality of the reaction cuvettes on the second measuring unit are dispensed with the biosamples on the first measuring unit, and wherein the plurality of the reaction cuvettes are subsequently transferred from the first measuring unit to the second measuring unit by the cuvette transfer means to stand thereon;
wherein at least one of the plurality of the reaction cuvettes is the reaction cuvette of claim 1; and
wherein different measurements are carried out by the first measuring unit and the second measuring unit.

9. The apparatus for a multiple automatic analysis of biosamples according to claim 8, wherein the measurement by the first measuring unit and the measurement by the second measuring unit are different from each other with respect to a measuring principle or a detection mode.

10. The apparatus for a multiple automatic analysis of biosamples according to claim 8, wherein the measurement carried out by the second measuring unit has a sensitivity or an accuracy higher than that of the measurement carried out by the first measuring unit.

11. The apparatus for a multiple automatic analysis of biosamples according to claim 8, wherein the measurement carried out by the first measuring unit is a biochemical or latex agglutination measurement, and the measurement carried out by the second measuring unit is an enzymatic immunoassay.

12. The apparatus for a multiple automatic analysis of biosamples according to claim 8, wherein each of the first measuring unit and the second measuring unit is a rotatable disc having a mounting zone capable of transporting the reaction cuvettes in a direction of rotation, in a peripheral region thereof, or a reciprocatable plate having a mounting zone capable of transporting the reaction cuvettes in a direction of reciprocation.

13. The apparatus for a multiple automatic analysis of biosamples according to claim 8, further comprising one or more additional measuring units fitted with an optical measuring means, and capable of detachably holding, in a mutually independent manner, a plurality of reaction cuvettes independent from each other, wherein a measurement different from those carried out by the first measuring unit and the second measuring unit is carried out thereby.

14. The apparatus for a multiple automatic analysis of biosamples according to claim 13, wherein the reaction cuvettes on the additional measuring unit are dispensed with the biosamples on the first measuring unit, and subsequently transferred from the first measuring unit to the additional measuring unit to stand thereon.

15. The apparatus for a multiple automatic analysis of biosamples according to claim 13, wherein the additional measuring unit is a rotatable disc having a mounting zone capable of transporting the reaction cuvettes in a direction of rotation, in a peripheral region thereof, or a reciprocatable plate having a mounting zone capable of transporting the reaction cuvettes in a direction of reciprocation.

16. The apparatus for a multiple automatic analysis of biosamples, according to claim 13, wherein the first measuring unit includes a first optical detector that is configured for a colorimetric or nephelometric measurement, the second measuring unit includes a second optical detector that is configured for a chemiluminescent measurement, and the additional measuring unit includes a third optical detector that is configured for a blood coagulation time measurement, and wherein the first, second and third optical detectors differ from one another.

17. The apparatus for a multiple automatic analysis of biosamples according to claim 13, wherein the first optical measuring means in the first measuring unit, the second optical measuring means in the second measuring unit, and one or more optical measuring means in one or more additional measuring units are optical detectors different from each other.

18. The apparatus for a multiple automatic analysis of biosamples according to claim 17, wherein the first optical measuring means in the first measuring unit, the second optical measuring means in the second measuring unit, and one of the optical measuring means in the one or more additional measuring units are optical detectors different from each other, and each of the detectors is any one of
   (1) an optical detector containing a light emission diode and a diode array,
   (2) an optical detector containing a lamp unit and a spectrometer, and
   (3) an optical detector containing a photomultiplier as a photodetector.

19. The apparatus for a multiple automatic analysis of biosamples according to claim 13, wherein the reagent supply unit further comprises a concentric ring reagent storing lane in which reagents to be supplied to the reaction cuvettes on one or more additional measuring units are stored.

20. The apparatus for a multiple automatic analysis of biosamples according to claim 8, further comprising one or more independent measuring units wherein the biosamples are supplied directly from the sample supply unit, and the measurement thereon can be conducted without a supply of any reagents from the reagent supply unit.

21. The apparatus for a multiple automatic analysis of biosamples according to claim 20, wherein the independent measuring unit includes an ion detector and is configured to measure body fluid electrolytes.

22. The apparatus for a multiple automatic analysis of biosamples according to claim 20, wherein at least one of the first measuring unit, the second measuring unit, and the one or more independent measuring units contains a means for detecting an abnormal sample.

23. The apparatus for a multiple automatic analysis of biosamples according to claim 20, wherein at least one of the first measuring unit, the second measuring unit, and the one or more additional measuring units contains a means for detecting an abnormal sample.

24. The apparatus for a multiple automatic analysis of biosamples according to claim 20, wherein the reagent supply unit further comprises a concentric ring reagent storing lane in which reagents to be supplied to the reaction cuvettes on one or more independent measuring units are stored.

25. The apparatus for a multiple automatic analysis of biosamples according to claim 8, wherein the reagent supply unit contains a plurality of concentric ring reagent storing lanes which are independently rotatable in a same or counter directions and stoppable, and reagents to be supplied to the reaction cuvettes on the first measuring unit and the second measuring unit are stored in each of the concentric ring reagent storing lanes, respectively.

26. The apparatus for a multiple automatic analysis of biosamples according to claim 8, wherein the reaction cuvette used has an arc-shaped mounting projection protruding from an upper sidewall of a cuvette main part.

27. The apparatus for a multiple automatic analysis of biosamples according to claim 26, wherein the reaction cuvette has a fixing projection protruding downward from an undersurface of the mounting projection.

28. The apparatus for a multiple automatic analysis of biosamples according to claim 8, wherein the parallel flat side walls of the main part of the cuvette comprise four parallel flat side walls.

29. The apparatus according to claim 8, further comprising a stirring device.

30. A method for a multiple automatic analysis of biosamples by an apparatus for a multiple automatic analysis of biosamples, said apparatus comprising
   a sample supply unit having a plurality of biosamples;
   a first measuring unit fitted with a first optical measuring means, said first measuring unit being capable of detachably holding, in a mutually independent manner, a plurality of reaction cuvettes independent from each other;
   a sample transport means capable of transporting the biosamples from the sample supply unit to one of the plurality of reaction cuvettes on the first measuring unit;
   a second measuring unit fitted with a second optical measuring means, said second measuring unit being capable of receiving a reaction cuvette transferred from the first unit and detachably holding, in a mutually independent manner, a plurality of reaction cuvettes independent from each other;
   a reagent supply unit having reagents for use in a measurement by the first measuring unit and in a measurement by the second measuring unit; and
   a reagent transport means capable of transporting reaction reagents, in a mutually independent manner, from the reagent supply unit to one of the plurality of reaction cuvettes on the first measuring unit and/or the second measuring unit,
   wherein the plurality of the reaction cuvettes on the second measuring unit are dispensed with the biosamples on the first measuring unit, and subsequently transferred from the first measuring unit to the second measuring unit by a cuvette transfer means to stand thereon;
   wherein at least one of the plurality of the reaction cuvettes is the reaction cuvette of claim 1; and
   wherein different measurements are carried out on the first measuring unit and the second measuring unit.

31. The method of claim 30, wherein the parallel flat side walls of the main part of the cuvette comprise four parallel flat side walls.

* * * * *

UNITED STATES PATENT AND TRADEMARK OFFICE
CERTIFICATE OF CORRECTION

PATENT NO.         : 9,341,640 B2
APPLICATION NO.    : 11/910408
DATED              : May 17, 2016
INVENTOR(S)        : Shintani et al.

It is certified that error appears in the above-identified patent and that said Letters Patent is hereby corrected as shown below:

On the title page item (73), Delete "MITSUBISHI KAGAKU IATRON, INC" and insert
-- LSI MEDIENCE CORPORATION --

Signed and Sealed this
Twenty-sixth Day of July, 2016

Michelle K. Lee
*Director of the United States Patent and Trademark Office*